United States Patent [19]

Bucalo

[11] 4,317,454

[45] Mar. 2, 1982

[54] METHODS AND DEVICES FOR OBTAINING SPECIMENS AND FOR SIGNALLING WHEN THE SPECIMEN HAS BEEN COLLECTED

[76] Inventor: Louis Bucalo, 155 Roberts St., Holbrook, N.Y. 11741

[21] Appl. No.: 165,052

[22] Filed: Jul. 1, 1980

Related U.S. Application Data

[63] Continuation of Ser. No. 821,749, Aug. 4, 1977, abandoned.

[51] Int. Cl.$^3$ .............................................. A61B 10/00
[52] U.S. Cl. ..................................... 128/759; 128/263
[58] Field of Search ............... 128/749, 756, 759, 769, 128/771, 284, 285, 287, 290 R, 263, 270

[56] References Cited

U.S. PATENT DOCUMENTS

| | | | |
|---|---|---|---|
| Re. 29,061 | 12/1976 | Bucalo | 74/339 |
| 2,002,368 | 5/1935 | Fancher | 128/290 R |
| 2,512,713 | 6/1950 | Cahill | 128/290 R |
| 2,943,979 | 7/1960 | Elias | 128/270 |
| 3,093,546 | 6/1963 | Atkinson | 128/290 R |
| 3,400,717 | 9/1968 | Cubitt et al. | 128/290 R |
| 3,794,024 | 2/1974 | Kokx et al. | 128/285 |
| 3,850,160 | 11/1974 | Denson | 128/270 |
| 3,948,257 | 4/1976 | Bossak | 128/285 |
| 3,952,347 | 4/1976 | Comerford et al. | 128/284 |
| 4,036,214 | 7/1977 | Bucalo | 128/769 |
| 4,059,404 | 11/1977 | Schuster et al. | 128/759 |

FOREIGN PATENT DOCUMENTS

| | | | |
|---|---|---|---|
| 2513941 | 9/1976 | Fed. Rep. of Germany | 128/759 |
| 905463 | 9/1962 | United Kingdom . | |

*Primary Examiner*—C. Fred Rosenbaum
*Attorney, Agent, or Firm*—Steinberg & Raskin

[57] ABSTRACT

In order to obtain information from a specimen which is initially present at a location such as part of a human being or other animal, there is situated at the latter location a device which includes a material which is capable of absorbing a specimen at the latter location and which with the specimen absorbed thereby can be introduced into a solvent in which the material dissolves while leaving in the solvent the specimen in a form capable of being analyzed. When used in connection with a living being, the device may include a signalling structure which signals the living being that the material has absorbed the specimen to an extent rendering removal of the device desirable, this signal to the individual being created by causing in response to contact with the collected specimen a sensation readily perceived by the living being or an observer.

4 Claims, 11 Drawing Figures

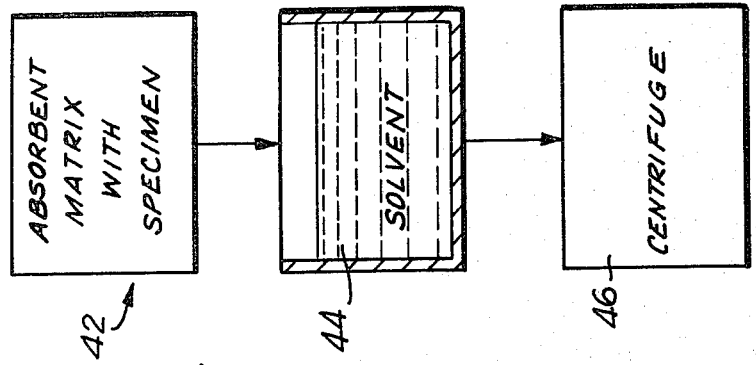
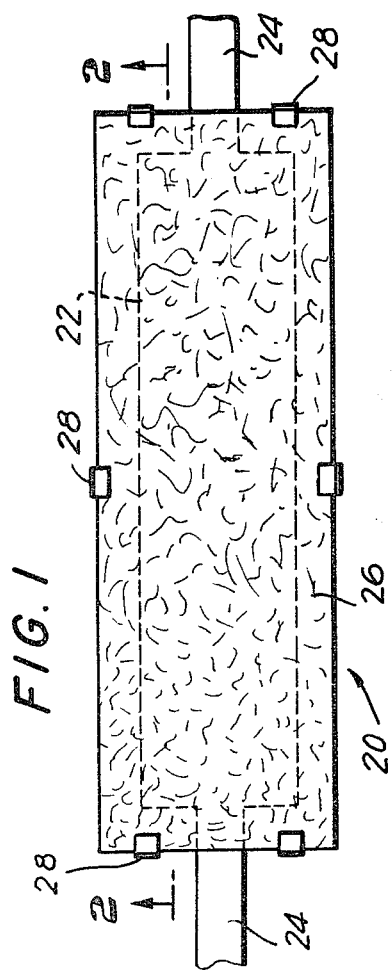
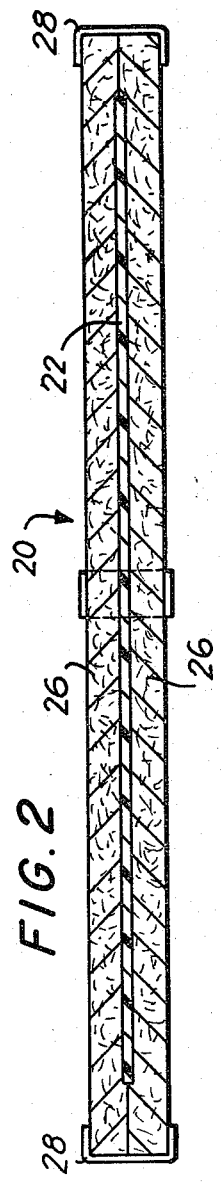
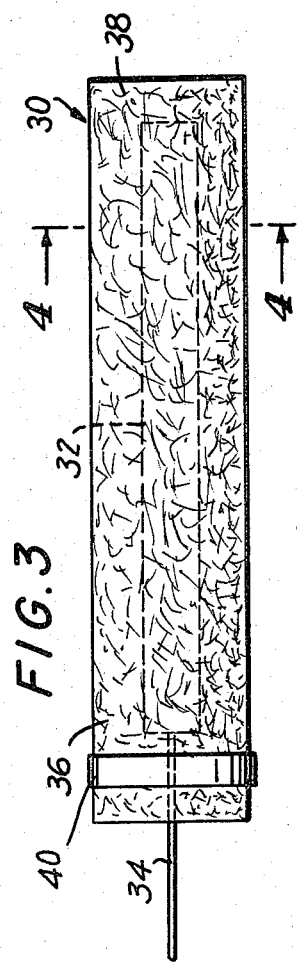
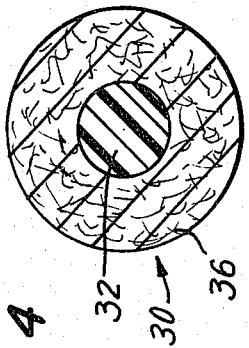

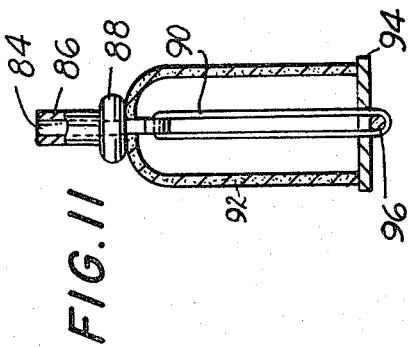
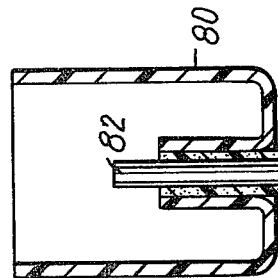
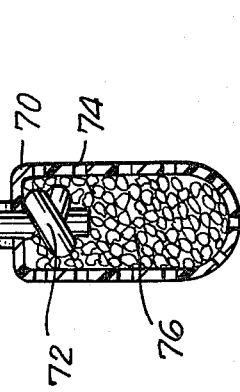
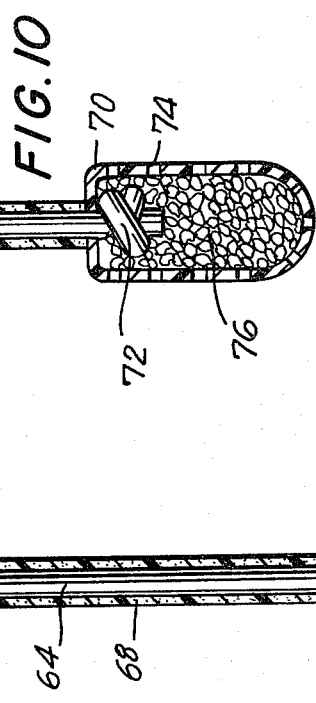
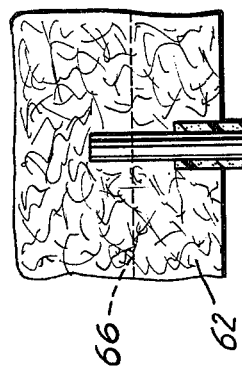

//<br>
METHODS AND DEVICES FOR OBTAINING SPECIMENS AND FOR SIGNALLING WHEN THE SPECIMEN HAS BEEN COLLECTED

This is a continuation of application Ser. No. 821,749, filed Aug. 4, 1977, now abandoned.

BACKGROUND OF THE INVENTION

The present invention relates to methods and devices for obtaining specimens from which it is possible to derive important information with respect to the source of the specimen, as well as to methods and devices for signalling when a specimen-collecting device should be removed.

As is well known, in order to obtain information-giving specimens from sources among which are parts of human beings or other animals, it is customary to situate at the source of the specimen a collecting device such as a suitable absorbent material. Thus, it is customary to use for such purposes porous bodies, cotton wadding, or the like. It is customary to obtain the specimen in different ways such as by wiping a swab across an area where a specimen is situated or by leaving at the location of the source of the specimen an absorbent medium which thereafter is removed with the specimen contained therein. At this stage it is necessary to remove the specimen from the device used to collect the same at the source of the specimen. For this purpose the collecting material may be squeezed so as to express a specimen therefrom, and the specimen extracted in this way may then be suitably analyzed, or the medium which has collected the specimen may be wiped across a microscope slide, for example, to provide on the slide a smear which is treated and examined in a known way to analyze the same.

Various problems are encountered with the above conventional devices and procedures. Thus, one of the most serious drawbacks encountered with conventional devices and procedures as set forth above is that only part of the collected specimen is utilized for analysis. Thus, when squeezing the specimen from the collecting device or when wiping the device across a slide, or a growth medium such as an agar dish, only part of the collected specimen is available for analysis while the remainder thereof remains in the collecting device. Very often it is precisely this remaining portion which is still contained by the collecting device which is of critical importance and which has the desired information whereas the part of the collected specimen which is used for analysis does not give the desired information.

Moreover, when utilizing that type of collecting device which remains at the source of the specimen, whether the specimen is to be used for analysis or is simply to be collected, it is at the present time difficult for a human being or observer to know when the collecting device has received the specimen to such an extent that it is desirable to remove the device. For example in connection with menstrual flow, whether the collected material is to be used for analysis or simply is to be collected and discarded, it is necessary for the female wearing a sanitary napkin or carrying a tampon to guess when the collecting device is to be removed so as to prevent undesirable staining of undergarments or other undesirable results.

SUMMARY OF THE INVENTION

It is accordingly a primary object of the present invention to provide methods and devices for solving the above problems.

Thus, it is an object of the present invention to provide a method and device according to which all of the collected specimen received by a means such as an absorbent medium is available for analysis.

In addition, it is an object of the present invention to provide methods and devices which make it possible to signal an individual when a specimen-collecting device should be removed or has become saturated.

In addition it is an object of the present invention to provide methods and devices of the above general type which are relatively inexpensive and at the same time highly effective for achieving the desired results.

According to the invention a method for obtaining information from a specimen which is initially present at a location such as part of a human being or other animal includes the step of situating at the latter location a material which is capable of absorbing a specimen at this location and which with the specimen absorbed thereby can be introduced into a solvent in which the material dissolves while leaving in the solvent the specimen in a more accessible form capable of being analyzed. In addition, in accordance with the invention a collecting means such as a suitable absorbing means has connected thereto a signalling means which will receive the collected material when the absorbing means has absorbed the collected material to a given extent. When the signalling means receives the collected material it provides automatically a sensation readily perceived by the individual or observer so as to indicate that the collecting device should be removed.

BRIEF DESCRIPTION OF DRAWINGS

The invention is illustrated by way of example in the accompanying drawings which form part of the application and in which:

FIG. 1 illustrates one possible embodiment of a device of the invention for carrying out a method of the invention;

FIG. 2 is a longitudinal sectional elevation of the structure of FIG. 1 taken along line 2—2 of FIG. 1 in the direction of the arrows;

FIG. 3 is a side elevation of another embodiment of a device of the invention for carrying out the method of the invention;

FIG. 4 is a transverse section of the structure of FIG. 3 taken along line 4—4 of FIG. 3 in the direction of the arrows;

FIG. 5 is a schematic flow diagram of one possible manner in which it is possible to take advantage of the features of the invention;

FIG. 6 is a fragmentary longitudinal sectional elevation of a further embodiment of a device and method of the invention for signalling when a specimen-collecting medium is saturated;

FIGS. 7 and 8 respectively illustrate different embodiments of devices utilizing the features of FIG. 6;

FIG. 9 is a fragmentary sectional elevation of another embodiment of a device and method of the invention for signalling when a collecting device is saturated;

FIG. 10 is a schematic sectional elevation of a further embodiment of a device of the invention for indicating when a collecting device is saturated; and FIG. 11 illustrates in a fragmentary partly sectional manner a further embodiment of a signalling means for signalling when a collecting device is saturated.

DESCRIPTION OF PREFERRED EMBODIMENTS

Referring to FIGS. 1 and 2, there is illustrated therein one possible embodiment of the device which is similar to a sanitary napkin. The illustrated device 20 has in its interior a flexible sheet 22 made, for example, of any suitable plastic. This sheet 22 has integral extensions 24 which are fragmentarily illustrated in FIG. 1 and which may be used for connecting the device to a belt. Thus, in connection with collection of vaginal fluids, including menstrual blood, the device 20 of the invention may be worn in the same way as a sanitary napkin.

In the particular example illustrated in FIGS. 1 and 2, the inner sheet 22 and part of the elongated strips 24 extending therefrom are situated between a pair of layers 26 of a collecting material according to the invention. These layers 26 may be held together, at least temporarily in any suitable way, as by utilizing short lengths of adhesive tape 28 which extend around the adjoining edges of the layers 26 in the manner apparent from FIGS. 1 and 2. The layers 26 are made of fibers so as to form a structure similar to layers of gauze, and these layers 26 will absorb material in much the same way as any porous or fibrous body, by capillary action. Thus, the device 20 may be situated at any location where there is a specimen which is to be collected for subsequent analysis. Although the particular structure shown in FIGS. 1 and 2 enables the device 20 to be used in the manner of a sanitary napkin as when it is desired to collect vaginal fluid or menstrual blood for analysis, it will be understood that the same type of device can be used for collecting any specimen from human beings or other animals as well as from any other source of a specimen which is to be collected and analyzed.

As is indicated in FIGS. 3 and 4, the device of the invention may take the form of a tampon. Thus, FIGS. 3 and 4 show a device 30 of the invention, this device including an inner core 32 which may be an elongated solid body or a hollow tubular body haveing closed ends, this core 32 being relatively flexible so that it will create no discomfort when situated in a body cavity. Fixed to one end of the body 32 is a string 34 which facilitates removal of the device 30 from a body cavity.

The core 32 and part of the string 34 are situated within a hollow sleeve 36 which has closed end 38 and an opposite open end, the sleeve 36 being made of a flexible material so that the open end can be gathered together and held by a tape 40 or the like, so as to maintain the core 32 reliably within the sleeve 36. This sleeve 36 may be made of a fibrous material or may be in the form of a porous body such as a foam matrix.

The device 30 may be inserted into the vagina to be used in a manner similar to a conventional tampon either for collecting vaginal fluids in general or for collecting menstrual blood. However, the device also may be used for other purposes. For example it may be introduced into the anus in order to collect rectal specimens which are to be analyzed, or the device can be situated at any location which forms the source of a specimen which is to be analyzed. For example, the device can be swallowed.

Thus, while the device 20 of FIGS. 1 and 2 and the device 30 of FIGS. 3 and 4 are illustrated as taking the form of a conventional sanitary napkin and tampon, respectively, it is to be understood that the device of the invention can take any configuration which is particularly adapted for the purpose of collecting a specimen from any source.

According to the invention the material used for the layers 26 or for the sleeve 36, while capable of effectively collecting a specimen, have the property of being dissolvable in a suitable solvent. Thus while these materials of layers 26 and sleeve 36 are inert with respect to the body or other location which forms the source for the specimen, so as not to influence the same and so as to remain uninfluenced thereby, they have the property of being capable of dissolving in a solvent which will not influence undesirably the specimen collected by the means formed by layers 26 or sleeve 36. For example, the layers 26 and sleeve 36 may be made of polycarbonate fibers which will dissolve in a solvent such as a chlorinated solvent solution such as chloroform. It is also possible to use for the layers 26 and sleeve 36 a styrene or styrofoam plastic which can be introduced into a chlorinated solvent solution such as chloroform or methylene chloride to dissolve therein. Also, the layers 26 and the sleeve 36 may be made of acetate fibers which will dissolve in a solvent such as acetone.

In addition it is possible to make the layers 26 and sleeve 36 of wax. For example a suitable wax material can have a fibrous form and be made into the layers 26 or the sleeve 36, with the wax having the property of remaining solid at body temperature while capable of collecting the specimen. Such as collecting means can simply be placed in water which is at a temperature high enough to cause the wax to dissolve. For example the wax may be made so as to remain uninfluenced by body temperatures while being dissolvable in water at a temperature of approximately 105° F. or somewhat higher.

With the above-described devices, after the specimen is collected by the means 26 or 36, the device 20 or 30 is removed from the source of the specimen with the specimen of course being carried by the means 26 or 36. Then, in the case of FIGS. 1 and 2, the tapes 28 are removed so that the layers 26 can simply be dropped into a solvent of the type referred to above. In the case of FIGS. 3 and 4 the tape 40 is removed and the core 32 together with the string 34 are separated from the sleeve 36 which is then simply placed in a solvent of the type referred to above. Thus, the collecting medium or means 26 or 36 will simply dissolve away in the solvent while leaving therein the collected specimen in a more accessible form capable of being analyzed.

It will be noted that as a result of the above features of the invention all of the specimen collected by the means 26 or 36 is retrievable for analysis. In the case of collecting menstrual fluid the accessibility of the entire specimen is absolutely necessary in order to make certain that the ovum is readily accessible in the analyzed specimen. There is only one ovum in the specimen, so that this ovum must be accessible for analysis and not discarded or lost in the collecting means.

According to a further feature of the invention it is possible to contact the collected specimen with an agent which will give the specimen a predetermined condition. Such an agent may be in the form of a suitable preservative, which may be citric acid when the collected specimen is blood, or the agent may be in the form of an antibiotic which will serve to kill certain microorganisms in the collected specimen in which there is no particular interest so that in this way those microorganisms which are of interest will be easier to identify. Such an agent may be placed in the collecting medium such as the layers 26 or the sleeve 36, before the specimen is collected thereby, or the agent may be applied to the collected specimen at the collecting means after the latter collects the specimen. For example if an individual collects a specimen in the home and mails it to a laboratory, the container for the absorbent medium with the specimen therein may be provided in its interior with an agent which contacts the collected specimen when the latter together with the absorbent medium are placed in the mailing container.

Solely by way of example there is shown in FIG. 5 an absorbent matrix 42 with the specimen contained therein, this matrix being for example either the layers 26 or the sleeve 36. This absorbent matrix 42 with the specimen contained therein is placed in the solvent solution 44 which is situated in a suitable container as illustrated. The collecting means simply dissolves away into the solution 44 while leaving in the latter the entire quantity of collected specimen. Then, for example, the solvent with the specimen therein is introduced into a filter system or a centrifuge 46 in which it is possible in a known way to separate from the solvent the material of the collected specimen such as cells thereof, or other components of the collected specimen, as is well known, the specimen which is separated in the centrifuge 46 then being available for analysis in a conventional manner.

It is thus apparent that with the method and device of the invention as described above and shown in FIGS. 1-5 no part of the specimen which is collected is lost. The entire collected specimen is available for analysis so that in this way if any component of collected specimen is of critical importance it will not, with the device and method of the invention, be retained by the collecting device.

It is to be noted that with the embodiments described above while the solvent can effectively dissolve the collecting means 26 or 36, it will have no undesirable influence on the collected specimen.

With specimen collecting devices of the type referred to above, and in fact with specimen collecting devices in general, such as conventional sanitary napkins and tampons, it is desirable to know when the device should be removed and, if necessary, replaced. For example in connection with menstrual flow, if a sanitary napkin or tampon is not removed in time, it can no longer absorb liquid with the result that undergarments become stained and other undesirable results may occur. In order to solve this problem the features illustrated in FIGS. 6-11 are provided in accordance with the present invention.

FIG. 6 fragmentarily illustrates in section any collecting or absorbent means 50 which may take the form of a conventional sanitary napkin 52 as shown in FIG. 7 or a conventional tampon 54 as shown in FIG. 8. Situated substantially centrally within the body 50 is a hollow capsule 56 made, for example, of a pair of tubular shells which are joined together in a well known manner. The capsule 56 has at the walls of its tubular shells openings 58 which pass through the shell walls so that liquid absorbed by the body 50, which may be liquid absorbed by the napkin 52 or tampon 54, will when reaching the innermost part of the collecting means pass through the openings 58 into the interior of the container formed by the capsule 56.

Situated within the container 56 are a plurality of crystals 60 which when contacted by the liquid will create a sensation which is readily perceived by the individual or animal utilizing the specimen-collecting device. For example, the crystals 60 may be crystals of potassium nitrate which, as is well known, react in the presence of a liquid such as blood or other liquids to produce a lowering of the temperature of the liquid to a temperature well below body temperature. Thus an individual or animal utilizing the device of the invention will feel the lower temperature created when the liquid contacts the crystals 60, and in this way a signal is provided indicating to the individual that the specimen collecting device should be removed. In the case of an animal, the behavior in response to the lower temperature is noted by an observer. Of course, this concept is of general utility and need not be used only in connection with sanitary napkins or tampons, and reliance need not be made only upon potassium nitrate crystals. For example the crystals 60 may take the form of perfume crystals which when contacted by the specimen will create a noticeable odor which signals the individual or observer that the specimen collecting device should be removed. The device which has the signalling means of the invention connected therewith may be, in addition to a tampon or a sanitary napkin, a suppository, a specimen swab, or any other similar device which is used for collecting specimens and which should be removed when the specimen has been collected to a given extent. An effervescent powder wick fizzes when contacted by the specimen may be used instead of the crystals 60.

According to the embodiment of the invention which is shown in FIG. 9, there is a specimen collecting means 62, which may take the form of any body of fibrous or porous material and may also be in the form of a sanitary napkin, tampon, suppository, or specimen swab. This body 62 has an elongated wick 64 fastened thereto. For example, the wick 64 may be fastened to the body 62 by a line of stitches 66. The wick 64 is encased at its portion which extends beyond the body 62 in a liquid-impervious sheath 68, which, for example, can take the form of a wax coating. At its end region distant from the body 62 the wick 64 has an enlargement in the form of a knot 70, or a suitable bead may be fastened to the wick for this purpose. This enlargement 70 is situated within a container 72 which may be made of a flexible springy plastic material having at its top end, as viewed in FIG. 9, an opening smaller than the enlargement 70 but capable of being spread over the enlargement 70 so as to contract behind the same, so as to fasten the container 72 with the wick 64 in such a way that part of the wick extends into the interior of the container 72. This container 72 may be made of any suitable springy plastic material such as polyethylene, for example. The wall of the container 72 is formed with a number of openings 74. In the interior of the container 72 are situated the crystals 76 which may be the same as the crystals 60. Thus these crystals 76 when contacted by the specimen will react to provide automatically a sensation which can easily be perceived by an individual. Thus if the crystals 76 are potassium nitrate, they will produce a temperature which is sufficiently low to be cold enough to be noticed by an individual. If they are in the form of perfume crystals they will create an odor easily perceived by an individual.

Thus, with the embodiment of FIG. 9 when the specimen has been absorbed by the body 62 to such an extent that the specimen has access to the part of the wick 64 which is in the interior of the body 62 beyond the sheath 68, this specimen will be sucked by the wick 64 so as to travel therealong into the container 72 into contact with the crystals 76 so as to create the sensation which is perceivable by the individual or to create in an animal behavior that can be easily observed. Of course when the structure of FIG. 9 is in the form of a sanitary napkin or tampon having the signalling means of FIG. 9 connected therewith, the container 72 will of necessity be situated next to a part of the body where the lower temperature, for example, can be readily perceived, or where the odor created will readily emanate to be sensed by the individual.

The embodiment of the invention which is illustrated in FIG. 10 has a signalling means which may be the same as that of FIG. 9. This in FIG. 10 the same reference characters are used in connection with the different parts of the signalling means. However in FIG. 10 this signalling means is shown operatively connected to a cervical cup 80 which is a known way can be introduced into the vagina to be situated next to the cervix for collecting uterine fluid. This fluid will rise up from the bottom of the cup 80 as the fluid continues to be collected, until the fluid contacts the exposed end 82 of the wick 64. Then this liquid will travel along the wick 64 through the liquid-impervious sheath 68 into the container 72 in order to reach the crystals 76 and react therewith to create the sensation which is readily perceived by the individual.

According to the embodiment of the invention which is illustrated in FIG. 11, there is a wick 84 which is fragmentarily illustrated and which may be the same as the wick 64 or the wick 82 and connected in the same way to specimen-collecting devices. This wick 84 is thus encased along most of its length within a liquid-impervious sheath 86 made of a suitable wax, for example, which is simply coated onto the exterior of the wick 84 along most of its length. The lower end of the wick 84 passes through a bead 88 which is clamped onto the wick in any suitable way, and beyond the bead 88 the free end of the wick 84 is connected to one end of an elastic member 90 which may take the form of a suitable rubber band, for example, and which forms a spring means of this embodiment. For example the lower end of the wick 84 may simply pass around part of the band 90 and be knotted. However, before being connected to the spring means 90 the wick 84 is passed through an opening which is formed in an end wall of a tubular member 92 which has an open end distant from the end through which the wick 84 passes. This member 92 may be made of a material which disintegrates or yields when contacted by the specimen but which otherwise is substantially rigid. For example the tubular member 92 may be made of a suitable gelatin.

Against the open end of the tubular member 92 there is a disc 94 formed with a central opening through which the elastic band 90 passes, this band 90 having fixed thereto a bead 96 or other enlargement which engages the disc 94 so as to press the latter against the open end of the tubular member 92 as a result of the force of the elastic band 90 which is stretched in the condition indicated in FIG. 11.

This construction shown in FIG. 11 operates in such a way that when the specimen travels through the wick 84 into contact with the member 92, the latter loses its rigidity, and the spring means, formed e.g. by the elastic band 90, suddenly contracts causing the disc 94 to be snapped forcibly against the end of the wick which is connected with the elastic band 90. This striking of the disc 94 against the end of the wick will create a noise as well as a vibration readily perceived by the individual carrying the specimen-collecting means so that the individual will in this way receive a sensation either by the sense of touch or the sence of hearing, or both, indicating that it is time to remove the collecting device. Of course, the bottom end of the wick 84 can be connected to a suitable metallic member which increase the noise or vibration. For example the bottom end of the wick 84 may be connected with a hook onto which the elastic band 90 is placed after passing through the opening of the disc 94. Of course in this case, as in FIG. 11, the elastic band 90 is in a stretched condition when placed on such a metallic hook against which the disc 94 will strike to give a noise and/or vibration indicating that the specimen-collecting device should be changed.

Thus, while any of the embodiments of FIGS. 6-11 can be used in connection with the devices of FIGS. 1-4 intended to collect a specimen, these devices of FIGS. 6-11 can also be used in general with any collecting devices for indicating by way of a suitable signal when the collecting device is saturated or should be removed and, if necessary, replaced. When the devices of FIGS. 6-11 are used by a human being, the signal will be perceived by the human being. However, when the devices of FIGS. 6-11 are used by non-human animals, a human observer can easily detect from the behavior of the animal that the sensation resulting from the signal has been perceived by the animal.

What is claimed is:

1. In a method for collecting a specimen present at a part of a living being, the steps of situating at said part of the being a means which will collect the specimen and which should be removed, and at least in some cases replaced, at a time when said means has collected the specimen to a given extent, and signalling the living being or an observer of the living being by a sensation which is readily perceived when said means have collected the specimen to said given extent and wherein the sensation is created by impacting a pair of elements against each other which impact is capable of being readily perceived.

2. A device for collecting specimens comprising material for collecting a specimen when situated at a living being wherein the specimen is present, and signalling means operatively connected with said material for automatically signalling by creating a sensation which is readily perceived when said material has collected a specimen to a given extent, said signalling means comprising bodies of potassium nitrate which automatically respond to the presence of sufficient specimen to create a reduced temperature which is perceivable by the living being.

3. A device for collecting specimens comprising material for collecting a specimen when situated at a living being where the specimen is present, and signalling means operatively connected with said material for automatically signalling by creating a sensation which is readily perceived when said material has collected a specimen to a given extent, said signalling means including a pair of members capable of being impacted against each other, spring means for urging said members together to impact them against each other, and yieldable means holding said members apart in opposition to said spring means and yielding when engaged by a specimen to release said spring means to impact said members against each other for creating a noticable noise or vibration.

4. A device for collecting specimens comprising material for collecting a specimen when situated at a living being where the specimen is present, and signalling means operatively connected with said material for automatically signalling by creating a sensation which is readily perceived when said material has collected a specimen to a given extent, said signalling means comprising an effervescent powder which fizzes when contacted by sufficient specimen so as to create an easily perceived sensation.

* * * * *